(12) United States Patent
Yevzlin et al.

(10) Patent No.: US 9,308,311 B2
(45) Date of Patent: Apr. 12, 2016

(54) ARTERIAL VENOUS SPOOL ANCHOR

(75) Inventors: Alexander S. Yevzlin, Black Earth, WI (US); Reed A. Houge, Buffalo, MN (US); Doug S. Wahnschaffe, Rogers, MN (US); Steve Berhow, Rogers, MN (US)

(73) Assignee: PHRAXIS, INC., St. Paul, MN (US)

(*) Notice: Subject to any disclaimer, the term of this patent is extended or adjusted under 35 U.S.C. 154(b) by 167 days.

(21) Appl. No.: 14/116,465

(22) PCT Filed: Jun. 15, 2012

(86) PCT No.: PCT/US2012/042639
§ 371 (c)(1),
(2), (4) Date: Nov. 8, 2013

(87) PCT Pub. No.: WO2012/174361
PCT Pub. Date: Dec. 20, 2012

(65) Prior Publication Data
US 2014/0088623 A1    Mar. 27, 2014

Related U.S. Application Data

(60) Provisional application No. 61/497,245, filed on Jun. 15, 2011, provisional application No. 61/497,254, filed on Jun. 15, 2011.

(51) Int. Cl.
*A61B 17/11* (2006.01)
*A61M 1/36* (2006.01)

(52) U.S. Cl.
CPC .............. *A61M 1/3653* (2013.01); *A61B 17/11* (2013.01); *A61M 1/3655* (2013.01); *A61B 2017/1107* (2013.01); *A61B 2017/1135* (2013.01)

(58) Field of Classification Search
CPC ........... A61B 17/11; A61B 2017/1107; A61B 2017/1135; A61B 2017/1103; A61B 2017/1132; A61B 2017/1121; A61B 17/1114; A61B 2017/00628; A61B 2017/00615; A61B 2017/00606; A61B 2017/00592; A61B 2017/00588; A61B 17/0057; A61M 1/3655; A61M 1/3653; A61M 1/14; A61F 2/86; A61F 2/915; A61F 2/95; A61F 2/82; A61F 2/07; A61F 2/06
USPC .......................................................... 606/153
See application file for complete search history.

(56) References Cited

U.S. PATENT DOCUMENTS 3,818,511 A    6/1974 Goldberg et al.
4,352,358 A *  10/1982 Angelchik ............. A61B 17/11
                                                    285/140.1

(Continued)

FOREIGN PATENT DOCUMENTS

CA    2366703 A1    9/2000
CA    2574941 A1    7/2007

(Continued)

OTHER PUBLICATIONS

Japanese Office Action issued by the Japanese Patent Office (translated), regarding corresponding patent application Serial No. 2014-516024, mailed Oct. 15, 2014; 5 pages.

(Continued)

*Primary Examiner* — Jonathan W Miles
*Assistant Examiner* — George J Ulsh
(74) *Attorney, Agent, or Firm* — Barbara A. Wrigley; Fox Rothschild LLP

(57) ABSTRACT

An anastomotic connector comprises a generally tubular main body having a distal end and a proximal end, and an anchor member integrally coupled to the distal end of the tubular main body. The anchor member includes first and second annular flanges that are movable from a first loaded position to a second expanded position. In the second expanded position, the annular flanges are substantially perpendicular to a longitudinal axis of the tubular main body portion.

15 Claims, 3 Drawing Sheets

(56) References Cited

U.S. PATENT DOCUMENTS

| | | |
|---|---|---|
| 4,368,736 A | 1/1983 | Kaster |
| 4,512,761 A | 4/1985 | Raible |
| 5,456,712 A | 10/1995 | Maginot |
| 5,755,775 A | 5/1998 | Trerotola |
| 5,755,778 A | 5/1998 | Kleshinski |
| 5,968,089 A | 10/1999 | Krajicek |
| 5,972,017 A | 10/1999 | Berg et al. |
| 6,030,395 A | 2/2000 | Nash et al. |
| 6,179,848 B1 | 1/2001 | Solem |
| 6,190,590 B1 | 2/2001 | Randall et al. |
| 6,210,429 B1 | 4/2001 | Vardi et al. |
| 6,241,743 B1 | 6/2001 | Levin et al. |
| 6,270,524 B1 | 8/2001 | Kim |
| 6,402,767 B1 | 6/2002 | Nash et al. |
| 6,451,048 B1 | 9/2002 | Berg et al. |
| 6,458,140 B2 | 10/2002 | Akin et al. |
| 6,464,665 B1 | 10/2002 | Heuser |
| 6,464,709 B1 | 10/2002 | Shennib et al. |
| 6,482,214 B1 | 11/2002 | Sidor et al. |
| 6,485,513 B1 | 11/2002 | Fan |
| 6,517,558 B2 | 2/2003 | Gittings et al. |
| 6,582,463 B1 | 6/2003 | Mowry et al. |
| 6,585,760 B1 | 7/2003 | Fogarty |
| 6,599,303 B1 | 7/2003 | Peterson et al. |
| 6,682,540 B1 | 1/2004 | Sancoff et al. |
| 6,719,781 B1 | 4/2004 | Kim |
| 6,743,243 B1 | 6/2004 | Roy et al. |
| 6,855,162 B2 | 2/2005 | Parodi |
| 7,025,773 B2 | 4/2006 | Gittings et al. |
| 7,056,326 B2 | 6/2006 | Bolduc et al. |
| 7,105,020 B2 | 9/2006 | Greenberg et al. |
| 7,175,652 B2 | 2/2007 | Cook et al. |
| 7,591,827 B2 | 9/2009 | Hill et al. |
| 7,611,523 B2 | 11/2009 | Vargas et al. |
| 7,691,140 B2 | 4/2010 | Bates et al. |
| 7,722,665 B2 | 5/2010 | Anwar et al. |
| 7,766,955 B2 | 8/2010 | Vardi et al. |
| 7,828,834 B2 | 11/2010 | Garbe |
| 7,850,725 B2 | 12/2010 | Vardi et al. |
| 7,892,247 B2 | 2/2011 | Conston et al. |
| 7,927,343 B2 | 4/2011 | Hill et al. |
| 8,287,586 B2 | 10/2012 | Schaeffer et al. |
| 8,298,251 B2 | 10/2012 | Golden et al. |
| 8,343,204 B2 | 1/2013 | Osborne |
| 8,361,092 B1 | 1/2013 | Asfora |
| 8,366,651 B2 | 2/2013 | Dakin et al. |
| 8,439,963 B2 | 5/2013 | Dickinson et al. |
| 8,486,153 B2 | 7/2013 | Levine et al. |
| 8,551,127 B2 | 10/2013 | Asfora et al. |
| 8,628,583 B2 | 1/2014 | Meade et al. |
| 8,715,336 B2 | 5/2014 | Chu et al. |
| 8,728,145 B2 | 5/2014 | Chuter et al. |
| 2002/0022853 A1 | 2/2002 | Swanson et al. |
| 2002/0099392 A1 | 7/2002 | Mowry et al. |
| 2002/0123790 A1 | 9/2002 | White et al. |
| 2003/0109893 A1 | 6/2003 | Vargas et al. |
| 2003/0144578 A1 | 7/2003 | Koster, Jr. |
| 2003/0216749 A1 | 11/2003 | Ishikawa et al. |
| 2004/0102794 A1 | 5/2004 | Roy et al. |
| 2004/0107004 A1 | 6/2004 | Levine et al. |
| 2004/0116946 A1 | 6/2004 | Goldsteen et al. |
| 2005/0137677 A1 | 6/2005 | Rush |
| 2005/0171598 A1 | 8/2005 | Schaeffer |
| 2005/0192604 A1 | 9/2005 | Carson et al. |
| 2005/0228409 A1 | 10/2005 | Coppi |
| 2005/0267559 A1 | 12/2005 | De Oliveira |
| 2007/0073388 A1 | 3/2007 | Krolik et al. |
| 2007/0106313 A1 | 5/2007 | Golden et al. |
| 2007/0179590 A1 | 8/2007 | Lu et al. |
| 2007/0185567 A1 | 8/2007 | Heuser et al. |
| 2007/0203572 A1 | 8/2007 | Heuser et al. |
| 2008/0082159 A1 | 4/2008 | Tseng et al. |
| 2008/0288044 A1 | 11/2008 | Osbourne |
| 2009/0036817 A1 | 2/2009 | Dakin et al. |
| 2009/0076587 A1 | 3/2009 | Cully et al. |
| 2009/0143793 A1 | 6/2009 | Chua et al. |
| 2009/0209855 A1 | 8/2009 | Drilling et al. |
| 2010/0010613 A1 | 1/2010 | Dorn |
| 2010/0036401 A1 | 2/2010 | Navia |
| 2010/0241218 A1 | 9/2010 | Bruszewski et al. |
| 2010/0280612 A1 | 11/2010 | Helmus |
| 2011/0031656 A1 | 2/2011 | Anneaux et al. |
| 2011/0118821 A1 | 5/2011 | Brocker et al. |
| 2011/0172684 A1 | 7/2011 | Granja Filho |
| 2011/0264196 A1 | 10/2011 | Savage et al. |
| 2011/0282368 A1 | 11/2011 | Swayze et al. |
| 2012/0065652 A1 | 3/2012 | Cully |
| 2012/0123513 A1 | 5/2012 | Asfora et al. |
| 2012/0290065 A1 | 11/2012 | Li et al. |
| 2013/0035752 A1 | 2/2013 | Chang |
| 2013/0274646 A1 | 10/2013 | Paris et al. |
| 2014/0031785 A1 | 1/2014 | Schwagten et al. |
| 2014/0121585 A1 | 5/2014 | Baker et al. |

FOREIGN PATENT DOCUMENTS

| | | |
|---|---|---|
| CA | 2766347 A1 | 12/2010 |
| CA | 2810671 | 3/2012 |
| JP | 2004-516914 A | 8/2002 |
| JP | 2006-510393 A | 2/2004 |
| JP | 2006-523515 A | 10/2006 |
| WO | WO 98-02099 A1 | 1/1998 |
| WO | WO-98-19629 A2 | 5/1998 |
| WO | WO-98-19636 A2 | 5/1998 |
| WO | WO 99-45861 A1 | 9/1999 |
| WO | WO 99-62415 A1 | 12/1999 |
| WO | WO 01-12074 A1 | 2/2001 |
| WO | WO 01-26562 A1 | 4/2001 |
| WO | WO 01-49213 A2 | 7/2001 |
| WO | WO 01-49213 A3 | 7/2001 |
| WO | WO-2004-010898 A1 | 2/2004 |
| WO | WO-2004-093966 A1 | 11/2004 |
| WO | WO 2006-028925 A1 | 3/2006 |
| WO | WO 2007-024964 A1 | 3/2007 |
| WO | WO 2008-157283 A1 | 12/2008 |
| WO | WO-2009-055651 A1 | 4/2009 |
| WO | WO 2010-121192 A1 | 10/2010 |
| WO | WO 2012-034108 A1 | 3/2012 |
| WO | WO 2012-117402 A1 | 9/2012 |

OTHER PUBLICATIONS

Japanese Office Action issued by the Japanese Patent Office (translated), regarding corresponding patent application Serial No. 2014-514937, mailed Oct. 15, 2014; 6 pages.

Japanese Office Action issued by the Japanese Patent Office (translated), regarding corresponding patent application Serial No. 2014-516037, mailed Oct. 15, 2014; 5 pages.

International Search Report, corresponding patent application Serial No. PCT/US2012/042639, dated Sep. 25, 2012; 2 pages, United States Receiving Office.

European Search Report issued by the European Patent Office, regarding correspondence patent application Serial No. 12799745.0; dated Feb. 12, 2015; 6 pages.

European Search Report issued by the European Patent Office, regarding correspondence patent application Serial No. 12800430.6; dated Feb. 17, 2015; 6 pages.

European Search Report issued by the European Patent Office regarding correspondence patent application Serial No. 12800335.7; dated Mar. 6, 2015; 6 pages.

International Search Report and Written Opinion issued by the ISA/U.S. Receiving Office, regarding corresponding application Serial No. PCT/US2012/042666; dated Sep. 13, 2012; 5 pages.

International Search Report and Written Opinion issued by the ISA/U.S. Receiving Office, regarding corresponding application Serial No. PCT/US2012/042688; dated Sep. 14, 2012; 9 pages.

International Search Report and Written Opinion issued by the ISA/U.S. Receiving Office, regarding corresponding application Serial No. PCT/US2012/067561; dated Apr. 22, 2013; 10 pages.

(56) References Cited

OTHER PUBLICATIONS

Japanese Rejection Office Action, issued by the Japanese Patent Office regarding corresponding patent application Serial No: 2015-517230; mailed Nov. 16, 2015; 8 pages (English translation).

Japanese Final Rejection Office Action, issued by the Japanese Patent Office regarding corresponding patent application Serial No. JP 2014-516024; mailed dated Jun. 4, 2015; 5 pages.

Japanese Final Rejection Office Action, issued by the Japanese Patent Office regarding corresponding patent application Serial No. JP 2014-514937; dated Jun. 10, 2015; 7pages.

Japanese Rejection Office Action, issued by the Japanese Patent Office regarding corresponding patent application Serial No. JP 2014-516037; dated Jun. 4, 2015; 8 pages.

* cited by examiner

ARTERIAL VENOUS SPOOL ANCHOR

BACKGROUND OF THE INVENTION

1. Field of the Invention

This invention relates to anastomotic connector devices. In particular, this invention relates to a vascular access device for use in hemodialysis and other procedures, such as in the cardiovascular field, where short-term and long-term access is required.

2. Background of the Related Art

In the United States alone, approximately 400,000 people have end-stage renal disease requiring chronic hemodialysis. Hemodialysis replaces kidney function by removing toxins from the blood that are normally removed by healthy kidneys. In order to effectively remove toxins, blood must be passed at a high blood flow rate through a hemodialysis machine. This high blood flow is best achieved by the creation of a permanent vascular access site that includes an arteriovenous (AV) anastomosis in which a vein is attached to an artery to form a high-flow shunt or fistula.

Typically, a vein may be directly attached to an artery, but it takes from six to eight weeks before the fistula has sufficiently matured (time between placement and cannulation for dialysis) to provide adequate blood flow for use with hemodialysis. Moreover, a direct anastomosis may not be feasible in all patients due to anatomical considerations. Other patients may require the use of artificial graft material to provide an access site between the arterial and venous vascular systems. Because of the length of time required for a fistula to mature a patient needing dialysis will typically require a temporary access device, such as a Quinton catheter, to be inserted for hemodialysis access until the fistula has matured. The use of a temporary catheter access exposes the patient to additional risk of bleeding and infection, as well as discomfort, and is associated with a 91% higher mortality rate compared to fistulas. In trying to increase the prevalence of fistulas in the U.S., a proportional rise in catheter use has been documented. What is needed is an improved vascular access device that addresses the foregoing problems.

BRIEF SUMMARY OF THE INVENTION

The present invention solves the foregoing problems by allowing a percutaneous connection to be created between an artery and vein in the arm of a kidney failure patient without the need for surgery; which allows immediate cannulation of the connection without reliance on catheter use; and which allows for the maturation of the outflow veins for subsequent conversion to a fistula.

In one aspect of the invention, an anastomotic connector is provided that includes a generally tubular main body having a distal end and a proximal end; and an anchor member integrally formed with the main body, the anchor member having first and second opposing annular flanges movable between a loaded position and an expanded position in which the annular flanges are substantially perpendicular to a longitudinal axis of the main body.

In another aspect of the present invention, a method of positioning an anastomotic connector within a fluid passageway includes (i) providing a generally tubular main body having a distal end and a proximal end; and an anchor member integrally formed with the main body, the anchor member having first and second opposing annular flanges movable between a loaded position and an expanded position in which the annular flanges are substantially perpendicular to a longitudinal axis of the main body; (ii) loading the anastomotic connector into an introducer; (iii) introducing a distal end of the introducer through an access site in a fluid passageway; and deploying the anastomotic connector into the fluid passageway, wherein upon deployment the first annular flange of the anchor member is expanded to engage an internal surface of the fluid passageway and the second annular flange engages an outer surface of the fluid passageway to seat the anastomotic connector in the fluid passageway.

These and other features of the invention will now be described in detail with reference to the accompanying Figures.

DETAILED DESCRIPTION OF THE INVENTION

The invention is generally directed to an anastomotic connector structured to attach a dialysis graft between an artery and a vein. The anastomotic connectors in accordance with the invention may be placed percutaneously or subcutaneously in either an artery or a vein, and may be fabricated from any biocompatible material suitable for implantation into the human body. Further, the anastomotic connectors preferably have a low cost and are readily replaceable. As will be appreciated by those of ordinary skill in the art based upon the following disclosure, the anastomotic connectors of the invention may replace the use of catheters in those patients on hemodialysis who are permanently consigned to catheter use due to their inability (anatomically or otherwise) to sustain long-term fistula or graft options.

Numerous structural variations of an anastomotic connector device are contemplated and within the intended scope of the invention. For purposes of discussion and not limitation, one exemplary embodiment will be described in detail below. As those of ordinary skill in the art will appreciate, although the anastomotic connector will be described with reference to placement within a vessel, it should be understood that the anastomotic connectors may be placed within various other fluid passageways without departing from the intended scope of the invention.

Figure 1:
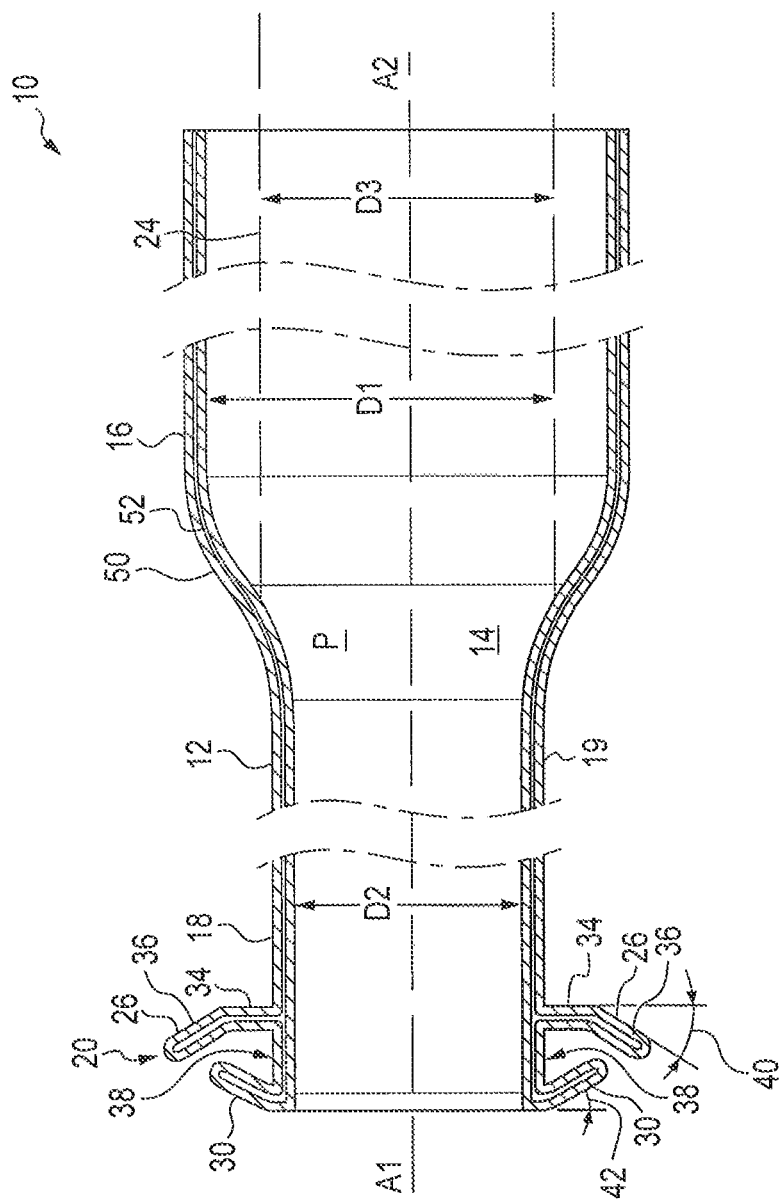
FIG. 1 is a side view of one exemplary embodiment of an anastomotic connector in accordance with the invention.

FIG. 1 is a side view of one exemplary embodiment of an anastomotic connector 10 in accordance with the invention. As illustrated in FIG. 1, anastomotic connector 10 generally includes a tubular main body 12 defining a lumen 14 therethrough thereby providing a fluid pathway P through anastomotic connector 10. Main body 12 includes first (proximal) 16 and second (distal) ends 18. In one exemplary embodiment, an internal diameter D1 of main body 12 may be greater at the first end 16 thereof than an internal diameter D2 at the second end 18 thereof to accommodate graft material 24. However, in other embodiments the internal diameter of first end 16 of main body 12 may be less than the internal diameter of second end 18, or the internal diameters may be substantially equivalent, without departing from the intended scope of the invention. The varying internal diameters of main body 12 may depend upon numerous factors such as, for example, the desired amount of flow through the connector 10. In exemplary embodiments the internal diameters of the anastomotic connector may range between about 1 mm and about 10 mm, although larger or smaller internal diameters are also contemplated and within the intended scope of the invention.

As illustrated in FIG. 1, anastomotic connector 10 may include a tubular graft 24 operably coupled to first end 16 of main body 12. A first internal diameter D3 of graft 24 is sized substantially equivalent to or slightly smaller than internal diameter D1 of main body 12 such that a fluid tight seal is formed between graft 24 and transition portion 17 main body 12.

Figure 3:
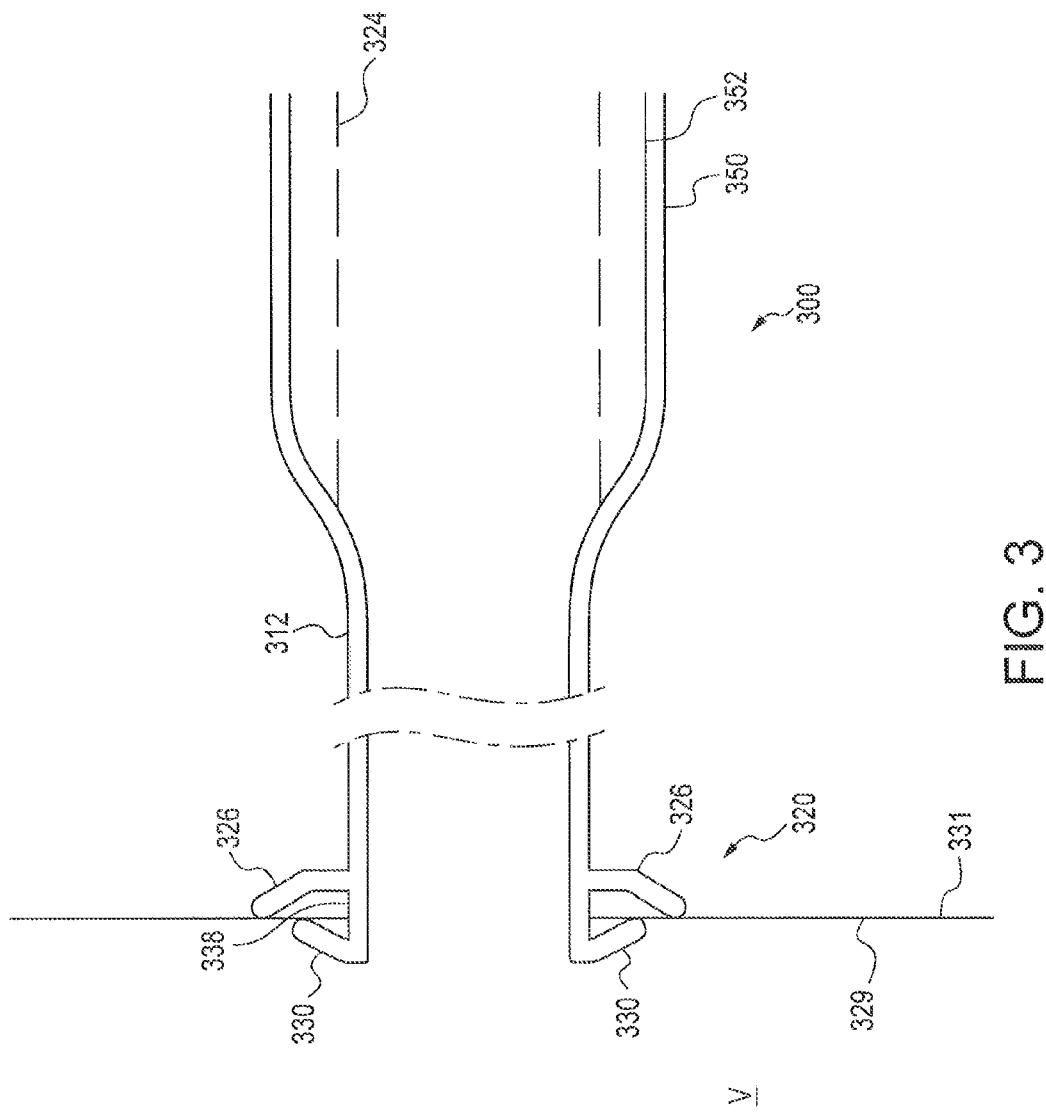
FIG. 3 illustrates anastomotic connector in accordance with the invention engaging an internal surface of a vessel.

As further illustrated in the exemplary embodiment of FIG. 1, first end (proximal) 16 of main body 12 integrally transitions into anchor member 20 through neck portion 19. Anchor member 20 includes opposing first and second annular flanges 30, 26 having central portion 38 disposed therebetween. Central portion 38 may vary in length depending on the width of vessel wall into which it will be deployed. First and second 30, 26 annular flanges are structured to move between a loaded position (not shown) prior to deployment and an expanded in situ position as illustrated in FIGS. 1 and 3. As will be appreciated by those of ordinary skill in the art, anchor member 20 is structured to provide a secure, leak-free connection to a vessel. Anchor member 20 may be either self-expanding or non-self-expanding. One benefit of using a self-expanding material is that annular flanges 30, 26 will expand when deployed within a vessel without the need for a separate expansion device, thus eliminating additional equipment and steps during the deployment process.

Annular flange 26 includes a first portion 34 and a second finger portion 36. First portion 34 extends from main body 12 substantially perpendicular to longitudinal axis A1. Finger portion 36 is offset from first portion 34 by acute angle 40 extending distally toward distal end 18 of main body 12. Second annular flange 30 is formed at the far distal end 18 of main body 12 and is offset from longitudinal axis A1 by acute angle 42 extending toward the proximal end 16 of main body 12. Acute angles 40, 42 may be substantially equivalent or may vary depending on numerous factors, without departing from the intended scope of the invention, so long as they are sufficiently angled to securely and firmly anchor anastomotic connector 10 to the vessel wall.

In forming an exemplary anastomotic connection in accordance with the invention a metal fabric is provided. The fabric is formed of a plurality of wire strands having a predetermined relative orientation between the strands. It is within the spirit of the invention that there may be numerous configurations that may be used for the wire strands, such as helical wherein the direction rotation of the wire strands are opposite one another; alternatively, the wire strands may be braided. Tubular braids are well known in the fabric arts and find some applications in the medical device field as tubular fabrics. As such braids are well known, they need not be discussed at length here.

The pitch of the wire strands (i.e. the angle defined between the turns of the wire and the axis of the braid) and the pick of the fabric (i.e. the number of turns per unit length) may be adjusted as desired for a particular application. For example, it is desirable that the anastomotic connector be formed to maintain a fair degree of flexibility and thus the pitch and pick of the fabric will tend to be lower as compared to a braid in which it is desirable to rigidly occlude fluid flow therethrough and the pitch and pick of the fabric is thus higher.

Figure 2:
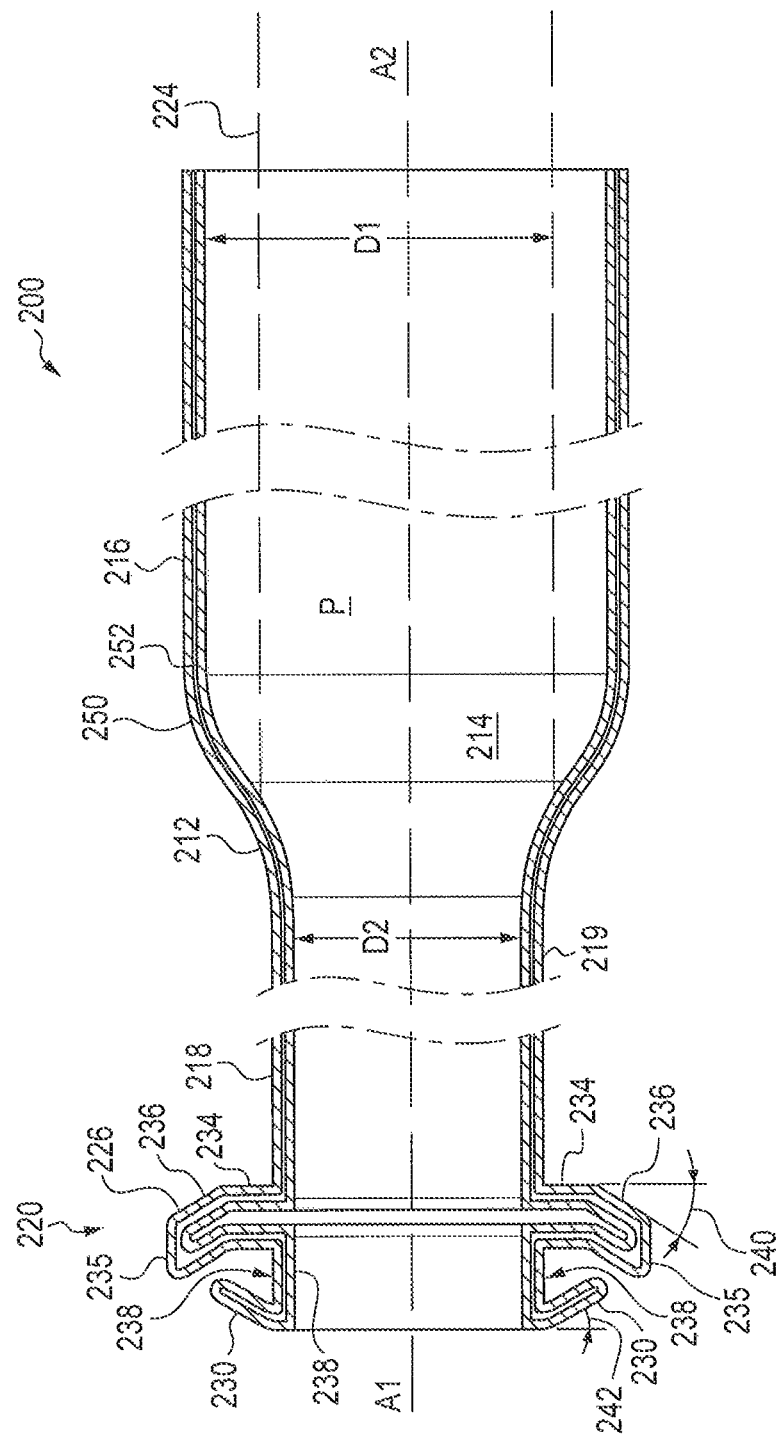
FIG. 2 is a side view of one exemplary embodiment of an anastomotic connector in accordance with the invention.

In forming the exemplary anastomotic connector 10, a tubular length of the braided metal fabric is inverted to form a double wall 50, 52 as best illustrated in FIGS. 1 and 2. As discussed previously, the wire strands of the metal fabric used in the exemplary anastomotic connector 10 should be formed of a material which is both resilient and which can be heat treated to substantially set a desired shape. The important factor in choosing a suitable material for the braided tubular structure is that the wires retain a suitable amount of the deformation induced by a molding surface (as described below) when subjected to a predetermined heat treatment.

One class of materials which meet these qualifications is so-called shape memory alloys. Such alloys tend to have a temperature induced phase change which will cause the material to have a preferred configuration which can be fixed by heating the material above a certain transition temperature to induce a change in the phase of the material. When the alloy is cooled back down, the alloy will "remember" the shape it was in during the heat treatment and will tend to assume that configuration unless constrained from so doing.

One particularly preferred shape memory alloy for use in the present method is Nitinol, an approximately stoichiometric alloy of nickel and titanium, which may also include other minor amounts of other metals to achieve desired properties. NiTi alloys such as nitinol, including appropriate compositions and handling requirements, are well known in the art and such alloys need not be discussed in detail here.

Such NiTi alloys are preferred, at least in part, because they are commercially available, have a high yield strain and more is known about handling such alloys than other known shape memory alloys. NiTi alloys are also very elastic—they are said to be "superelastic" or "pseudoelastic." This elasticity will help a device of the invention return to a present expanded configuration for deployment into a blood vessel. However, any suitable self-expanding material may be used as will be appreciated by those of ordinary skill in the art.

In forming the exemplary anastomotic connector of the invention, an appropriately sized piece of the metal fabric is cut from the larger piece of fabric which is formed, for example, by braiding wire strands to form a long tubular braid. The dimensions of the piece of fabric to be cut will depend, in large part, upon the size and shape of the connector to be formed therefrom. It is contemplated that the size and shape of the connector may vary depending on whether the use is for adults or children.

When cutting the fabric to the desired dimensions, before and/or after inversion, care should be taken to ensure that the fabric will not unravel. In the case of tubular braids formed of NiTi alloys, for example, the individual wire strands will tend to return to their heat-set configuration unless constrained. If the braid is heat treated to set the strands in the braided configuration, they will tend to remain in the braided form and only the ends will become frayed. However, it may be more economical to simply form the braid without heat treating the braid since the fabric will be heat treated again in forming the medical device. Alternatively, one can solder, braze, spot, laser treat or otherwise affix the ends of the desired length together (e.g. with a biocompatible cementitious organic material) before forming the connector.

Once an appropriately sized piece of the tubular metal fabric is obtained, it is inverted onto itself and deformed to generally conform to a surface of a molding element. As will be appreciated more fully from the discussion below, so deforming the fabric will reorient the relative positions of the strands of the metal fabric from their initial order to a second, reoriented configuration. The shape of the molding element should be selected to deform the fabric into substantially the shape of the exemplary anastomotic connector.

The molding element can be a single piece, or it can be formed of a series of mold pieces which together define the surface to which the fabric will generally conform. The molding element can be positioned within a space enclosed by the fabric or can be external of such a space, or can even be both inside and outside such a space.

It is also contemplated that a woven material may be used between walls 50, 52 to ensure a leak-tight seal when implanted in the body. The woven material may be chosen to promote tissue in-growth or not. It is desirable that the material be fluid non-permeable or impermeable. Alternatively, after forming the anastomotic connector as described above, a fluid impermeable, biocompatible polymer may be deposited between walls 50, 52. Such a polymer will thus fill the interstices of the braided metal material ensuring a leak-tight seal. Such biocompatible materials may include, but are not limited to, expanded Polytetrafluoroethylene ("ePTFE"), polyester, silicone composites, or various other plastics and elastomers or combinations thereof.

FIG. 2 is an alternative, exemplary embodiment of an anastomotic connector 200 in accordance with the invention. Anastomotic connector 200 is substantially similar to connector 10 depicted in FIG. 1 as like numerals indicate. Most notably, however, anchor member 220 includes first annular flange 230; second annular flange 226; and central portion 238 disposed therebetween. Central portion 238 may vary in length depending on the vessel wall into which it will be deployed. First and second 230, 226 annular flanges are structured to move between a loaded position (not shown) prior to deployment and an expanded in situ position as illustrated in FIGS. 2 and 3. As will be appreciated by those of ordinary skill in the art, anchor member 220 is structured to provide a secure, leak-free connection to a vessel. Anchor member 220 may be either self-expanding or non-self-expanding.

Annular flange 226 includes a first portion 234 and a second finger portion 236. First portion 234 extends from main body 212 substantially perpendicular to longitudinal axis A1. Finger portion 236 includes a substantially flat head and is offset from first portion 234 by acute angle 240. Finger portion extends toward the distal end 218 of main body 212. Substantially flat head 235 is designed to allow anchor member 220 to lay flat against a vessel wall after deployment for increased stability and seating in the vessel and along the vessel wall.

FIG. 3 is a diagram illustrating an exemplary anastomotic connector 300 deployed within a vessel V. Particularly, after anastomotic connector 300 is deployed within vessel V, annular flanges 330, 326 of anchor member 320 are moved to the expanded position (either due to the shape memory properties or by mechanical actuation) to secure the connector 300 to vessel V. As shown in FIG. 3, in the expanded position first annular flange 330 engages an inner surface 329 of vessel V while second annular flange 326 engages an outer surface of the vessel wall 331. Central portion 338 is shown as lying in a plane generally perpendicular to the vessel wall 329, 331 merely for purposes of example and not by limitation. In order to provide a fluid tight seal between anastomotic connector 300 and vessel V, it is contemplated that connector 300 will contain fabric or fibers within walls and/or be coated with a polymeric coating as discussed in detail hereinbefore.

Additionally, it may be preferable to provide the anastomotic connectors of the invention with an inner surface that is contoured to allow smooth arterial or venous blood flow into and out of the connector device. As those of ordinary skill in the art will appreciate, providing a non-thrombogenic surface minimizes the creation of recirculation or stagnation zones with high shear or dwell times that could otherwise lead to clotting.

It is also contemplated that the inner or outer surface of the anastomotic connectors of the invention be configured to deliver and release therapeutic substances such as anti-microbial agents, anti-inflammatory agents, anti-proliferative agents (e.g. taclipaxel), growth factors, stem cells, collagen and the like. Those of ordinary skill in the art will appreciate that these therapeutic agents may be coupled with the connector and/or the external or internal surface of the connector by means such as being encased or embedded in a polymeric or other biocompatible coating, applied to a textured external surface of the connector; contained within pockets of the connector on either an internal or external surface, and the like.

Although anchor members 20, 220 and 320 are described as including "annular flanges," other anchoring structures, such as hooks, barbs, tines and other types of curved or angled fasteners, are contemplated as will be appreciated by those of ordinary skill in the art.

Referring by way of example to FIG. 3, and as will be discussed in further detail to follow, a first anastomotic connector 300 may be implanted through the sidewall of an artery in such a way that first annular flange 330 engages an inner surface 329 of vessel V while second annular flange 326 engages an outer surface of the vessel wall and main body 312 protrudes through the sidewall of the vessel V at the site of implant. A second anastomotic connector 300 may be implanted through the sidewall of a vein in such a way that first annular flange 330 engages an inner surface 329 of vessel V while second annular flange 326 engages an outer surface of the vessel wall and main body 312 protrudes through the sidewall of the vessel V at the site of implant. A dialysis or vascular access graft, such as graft 324, may be coupled to the first and second anastomotic connectors such that graft end 53 lies adjacent transition area 317 thus providing a fluid pathway between the vein and the artery. One exemplary but non-limiting type of graft that may be used is a Vectra® vascular access graft (BARD Peripheral Vascular, Tempe, Ariz.).

More particularly, in one exemplary method of positioning or deploying anastomotic connectors in accordance with the invention, the connectors may be deployed with a catheter type introducer mechanism. For example, a needle access aperture may first be made into the target artery through the intended implant site of the connector. A guidewire may then be guided through the inserted needle. Once the guidewire is fully inserted, the needle may be retracted while leaving the guidewire in position. Next, an introducer that is "pre-loaded" with an anastomotic connector may be slid over the guidewire. After the anastomotic connector is positioned within the artery, the particular anchor member associated with the connector may be deployed. As will be appreciated by those of ordinary skill in the art, when non self-expanding anchor members are utilized, the introducer may include an expansion means.

An introducer may be pre-loaded with any of anastomotic connectors 10, 200, 300. The anastomotic connector 10, 200, 300 is then introduced into a target vessel V (post needle and guidewire insertion). During deployment into vessel V, first and second opposing annular flanges expand. First annular flange 30, 230, 330 is expanded or self-expands to engage an inner surface 329 of vessel V while second annular flanges 26, 226, 326 is expanded or self-expands to engage an outer surface 331 of the vessel wall to anchor connector 10, 200, 300 to vessel V. While anastomotic connector 10, 200, 300 is being deployed, the physician may verify that the connector placement is accurate by feeling the resistance of the first annular flange 30, 230, 330 against the inner surface of the vessel wall. As will be appreciated by those of ordinary skill in the art, after deployment the engagement of the respective annular flanges with the inner surface of the vessel V functions to securely maintain the anastomotic connector in fluid-tight engagement at the desired implantation site. After the anastomotic connector 10, 200, 300 has been properly secured to vessel V, the physician may attach graft 24, 224, 324 to main body 12, 212, 312.

The above-described process is then repeated in a second fluid passageway with a second anastomotic connector. A second anastomotic connector is coupled to a graft to create fluid communication between the first and second fluid passageways through the graft.

As will be appreciated by those of ordinary skill in the art, the same general process described above may be followed in order to place a connector within other types of fluid passageways. Although a method of deploying an anastomotic connector having a self-expanding anchor member has been generally described herein, the method may be adapted for deploying an anastomotic connector having a non self-expanding anchor member.

Based upon the present disclosure and after viewing the exemplary embodiment of the anastomotic connector presented herein, the many advantages and benefits provided by the invention will be appreciated by those of ordinary skill in the art. One advantage is that the geometry of the anastomotic connector allows continuous and uninterrupted arterial or venous flow during use for dialysis or other applications, thereby eliminating or substantially reducing any loss of circulation to the downstream, distal extremities. Stated alternatively, the geometry of the anastomotic connectors allows "full" flow into the graft as well as "full" flow to the downstream anatomy. Thus, distal arterial flow is not "cut-off" due to the presence of the anastomotic connector. Another advantage is that the anastomotic connectors of the invention may be implanted percutaneously rather than with an "open surgery" approach. The implantation method is therefore less invasive for the patient and faster for the surgeon. Yet another advantage is that the present invention allows for maturation of the distal vein in preparation for secondary AVF while avoiding a central dialysis catheter.

Although the present invention has been described with reference to preferred embodiments, workers skilled in the art will recognize that changes may be made in form and detail without departing from the spirit and scope of the invention.

What is claimed is:

1. An anastomotic connector comprising: a generally tubular main body having a distal end and a proximal end; and an anchor member integrally formed with the main body, said anchor member comprising first and second opposing annular flanges movable between a loaded position and an expanded position wherein said first and second opposing annular flanges are substantially perpendicular to a longitudinal axis of the main body, wherein an entirety of the tubular main body and said anchor members are integrally formed from a metal fabric configured to be inverted to form a double wall, wherein said first annular flange includes a first portion and a second finger portion, wherein said first portion is substantially perpendicular to a longitudinal axis of said main body, wherein said second finger portion is offset from said first portion by an acute angle, wherein said second finger portion extends toward the distal end of the main body.

2. The anastomotic connector of claim 1 wherein an internal diameter of the main body is greater at the proximal end than at the distal end.

3. The anastomotic connector of claim 1 wherein the anchor member further includes a central portion positioned between the first annular flange and the second annular flange, said central portion configured to extend between an inner surface and an outer surface of a fluid passageway.

4. The anastomotic connector of claim 1 wherein said connector comprises a self-expanding material.

5. The anastomotic connector of claim 1 wherein said second annular flange extends proximally toward the proximal end of the main body and is offset from a longitudinal axis of the main body by an acute angle.

6. The anastomotic connector of claim 1 wherein the metal fabric comprises a plurality of wire strands having a predetermined relative orientation between the strands.

7. The anastomotic connector of claim 6 wherein the wire strands are helically configured.

8. The anastomotic connector of claim 6 wherein the wire strands are braided.

9. The anastomotic connector of claim 6 wherein a pitch and pick of the wires is low.

10. The anastomotic connector of claim 6 wherein a pitch and pick of the wires is high.

11. The anastomotic connector of claim 1 wherein said metal fabric is configured to retain an effective amount of deformation induced by a molding surface when subjected to a predetermined amount of heat.

12. The anastomotic connector of claim 11 wherein said fabric is a shape memory alloy.

13. The anastomotic connector of claim 12 wherein said fabric is Nitinol.

14. The anastomotic connector of claim 1 wherein said second annular flange includes a substantially flat head.

15. A method of positioning an anastomotic connector within a fluid passageway comprising: providing an anastomotic connector having a generally tubular main body including a distal end and a proximal end and an anchor member integrally coupled to the main body, said anchor member comprising a first and second opposing annular flanges movable between a loaded position and an expanded position wherein the first and second opposing annular flanges are substantially perpendicular to a longitudinal axis of the main body, wherein an entirety of the tubular main body and said anchor members are integrally formed from a metal fabric configured to be inverted to form a double wall: loading the anastomotic connector into an introducer; introducing a distal end of the introducer through an access site in a fluid passageway; and deploying the anastomotic connector into the fluid passageway, wherein upon deployment one annular flange of the anchor member expands to engage an internal surface of the fluid passageway and the second annular flange expands to engages an outer surface of the fluid passageway to seat the anastomotic connector in the fluid passageway, wherein said first annular flange includes a first portion and a second finger portion, wherein said first portion is substantially perpendicular to a longitudinal axis of said main body, wherein said second finger portion is offset from said first portion by an acute angle, wherein said second finger portion extends toward the distal end of the main body.

* * * * *